United States Patent [19]

Farris et al.

[11] Patent Number: 5,538,506
[45] Date of Patent: Jul. 23, 1996

[54] PREFILLED FLUID SYRINGE

[76] Inventors: Barry Farris, P.O. Box 1990, Pollock Pines, Calif. 95726; Bernhard Kreten, 77 Cadillac Dr., #245, Sacramento, Calif. 95825

[21] Appl. No.: 147,128

[22] Filed: Nov. 3, 1993

[51] Int. Cl.⁶ .................................................. A61M 5/00
[52] U.S. Cl. .......................... 604/187; 604/212; 604/217; 222/94
[58] Field of Search ..................... 604/212–217, 604/905, 200, 207, 187, 185, 131, 132, 133, 142, 148, 190, 192, 197, 263, 403, 404, 407, 410; 222/92, 94, 95, 97, 129, 130, 147

[56] References Cited

U.S. PATENT DOCUMENTS

| | | | |
|---|---|---|---|
| D. 246,321 | 11/1977 | Löfman | 604/216 |
| 1,643,531 | 9/1927 | Wolf . | |
| 1,762,430 | 6/1930 | Tokita . | |
| 2,667,165 | 1/1954 | Smith . | |
| 2,667,872 | 2/1954 | Smith . | |
| 2,744,527 | 5/1956 | Barrett et al. . | |
| 2,744,528 | 5/1956 | Barrett et al. . | |
| 2,748,770 | 6/1956 | Moeck . | |
| 2,768,623 | 10/1956 | Marchand . | |
| 2,881,953 | 4/1959 | Kuschel | 222/94 |
| 2,911,972 | 11/1959 | Elinger . | |
| 3,078,847 | 2/1963 | Wandell et al. . | |
| 3,089,489 | 5/1963 | Dunmire . | |
| 3,261,381 | 7/1966 | Roach | 222/94 |
| 3,335,914 | 8/1967 | Strazdins et al. | 222/107 |
| 3,340,869 | 9/1967 | Bane . | |
| 3,557,788 | 1/1971 | Swartz . | |
| 3,712,295 | 1/1973 | Kline . | |
| 3,736,933 | 6/1973 | Szabo . | |
| 3,938,514 | 2/1976 | Boucher | 604/216 |
| 4,018,222 | 4/1977 | McAleer et al. . | |
| 4,130,117 | 12/1978 | Van Eck . | |
| 4,168,032 | 9/1979 | Sneider . | |
| 4,248,227 | 2/1981 | Thomas | 604/212 |
| 4,282,986 | 8/1981 | af Ekenstam et al. | 222/1 |
| 4,357,937 | 11/1982 | Burrell, Jr. et al. . | |
| 4,411,656 | 10/1983 | Cornett, III | 604/212 |
| 4,502,616 | 3/1985 | Meierhoefer | 604/200 |
| 4,548,601 | 10/1985 | Lary | 604/204 |
| 4,610,670 | 9/1986 | Spencer | 604/29 |
| 4,753,638 | 6/1988 | Peters | 604/212 |
| 4,955,871 | 9/1990 | Thomas | 604/217 |
| 4,966,312 | 10/1990 | Waring | 604/216 |
| 4,994,039 | 2/1991 | Mattson | 604/408 |
| 5,102,398 | 4/1992 | Farris | 604/212 |
| 5,215,221 | 6/1993 | Dirksing | 222/94 |
| 5,242,422 | 9/1993 | Schneberger et al. | 604/216 |

FOREIGN PATENT DOCUMENTS

| | | | |
|---|---|---|---|
| 278032 | 12/1965 | Australia . | |
| 470700 | 4/1914 | France . | |
| 1316596 | 12/1962 | France . | |
| 1330410 | 5/1963 | France | 604/212 |
| 2058585 | 5/1971 | France . | |
| 446819 | 7/1927 | Germany . | |
| 556491 | 8/1932 | Germany . | |
| 0577611 | 6/1933 | Germany | 604/216 |
| 3827335 | 2/1990 | Germany . | |
| 0092396 | 10/1959 | Netherlands | 604/212 |
| 0279468 | 3/1952 | Switzerland | 604/212 |
| 1553135 | 3/1990 | U.S.S.R. | 604/131 |
| 0386298 | 2/1933 | United Kingdom | 222/95 |
| 557400 | 11/1943 | United Kingdom . | |
| 8701944 | 4/1987 | WIPO | 604/212 |

*Primary Examiner*—John D. Yasko
*Assistant Examiner*—Ronald K. Stright, Jr.
*Attorney, Agent, or Firm*—Bernhard Kreten

[57] ABSTRACT

A syringe which has been prefilled to include a prescribed liquid and also a gas. The syringe includes a reservoir, a chamber which is in fluid communication with the reservoir and an outlet which is interposed between the chamber and the reservoir. Severing the chamber from the reservoir at the outlet will provide a syringe that includes a reservoir and an outlet. Prior to severing the chamber from the reservoir, the syringe may first be oriented such that all gas is directed into the chamber so that the syringe's reservoir will be completely filled with non-compressible fluid such as the medicating liquid.

32 Claims, 6 Drawing Sheets

PREFILLED FLUID SYRINGE

FIELD OF THE INVENTION

The following invention relates generally to dose administering devices. More specifically, the following invention is directed to a syringe which is prefilled with a liquid that can be used either in a needleless system or with needles to administer fluids in a medical environment.

BACKGROUND OF THE INVENTION

Conventional syringes provide frequent risk when manipulated in their intended use, also unfortunately sometimes during unintended reuse and always during disposal. In using a conventional syringe, the syringe is packaged empty and must be filled by fluid communication with an ampoule. The ampoule is configured as a container sealed by a rubber dam which is to be perforated by a needle attached to the syringe.

The contents within the ampoule is in an air-tight container. Consequently, one extracting a dose of fluid from the ampoule will generate a negative pressure if the syringe is first inserted into the ampoule while the piston of the syringe is in a fully "closed" position, i.e. no air space exists between the piston and the needle carried on the cylinder. As a result, many people who use syringes to extract fluids from ampoules will begin with the piston of the syringe in an intermediate position and push air into the ampoule creating a positive pressure. This makes it easier to withdraw fluid from the ampoule.

It is to be noted, however, that the air that is thus injected into the ampoule is a contaminant, since normal air in an every day environment is filled with particulate contaminants which necessarily become transmitted into the ampoule. In a medical care environment, such as in a hospital or doctor's office, it may even be more likely that the contaminant could foster pathogens. Thus, subsequent users of the ampoule are faced with the real possibility that a contaminant injected into the ampoule during a prior excursion into the ampoule will be passed onto a subsequent user of the medication.

Since the conventional syringe utilizes a piston which reciprocates within a cylinder, the conventional syringe adapts itself to reuse multiple times. There is no impediment inherent in the construction of a syringe which precludes its subsequent use by others. It is common knowledge and has been widely reported that reuse by third parties provides unwanted risks in spreading disease.

Another problem associated with an ampoule-type of system involves the requirement that the dose administrator exercise extreme care in aligning the needle at all times, such as with respect to the rubber dam of the ampoule. Inadvertent needle sticks can have dire consequences.

In all cases, in order to effectively utilize the syringe, the needle must first have been placed on the syringe body. This is typically performed by a luer coupling which unites a base of the needle to a tip of the syringe. Once the syringe has been equipped with the needle, extraordinary care must be exercised to prevent unwanted needle sticks such as described earlier. Frequently, the syringe is loaded with medicating fluid at a site remote from the patient who is to receive the dose. When this is the case, a syringe equipped with a needle must be transported to the patient. Most systems provide for a needle cap to be placed back over the needle to guard against unintended contact. Problems with inadvertent needle sticks when replacing a needle cap are quite common.

Even after "uneventful" utilization of the syringe on the patient, the problems associated with disposal of the needle and syringe are more complex since this system has now been further compromised by contact with the patient. Extraordinary attempts in adequately disposing of hazardous medical waste, including used syringe and needle systems are well documented in both the patent literature, the media, the medical literature and elsewhere.

It appears that a solution to the longstanding problem of disposing of medical wastes continues to evade resolution both as to individual use and as to hazardous waste treatment despite strong incentives now in place in the medical community to minimize the need for and utilization of needles whenever possible. One result has been a trend to embrace needleless systems whenever possible or to tailor systems which call for infrequent needle use.

One common scenario that lends itself to a substantially "needleless" systems involves patients in medical facilities such as hospitals who receive periodic doses of liquids intravenously. It is quite common to install a catheter in a patient intravenously and then access the catheter for subsequent doses of liquid rather than search for another site for each subsequent injection. Unfortunately, many systems using catheters still require the use of a syringe equipped with a needle in order to access the catheter itself.

Another problem with accessing a catheter is that it is used intermittently. There is a natural tendency of the patient's system to view the installed catheter as the foreign body that it is. Therefore, the site where the catheter communicates with the blood in a vein is susceptible to clotting. Administering liquid when the outlet end of the catheter has partially clotted closed increases the likelihood that a blood clot would be dislodged from the catheter and sent coursing through the venous system of the body. Consequently, extreme care is required when administering a dose through a syringe via a catheter in order to sense the presence of a restriction which suggests a clot at the outlet end of the catheter. Experienced personnel should perceive increased back-pressure or resistance when advancing the plunger of the piston within the cylinder. Sensing back-pressure is somewhat intuitive and certainly benefits from experience.

A certain degree of tactile feedback can be perceivable when using a conventional syringe. Since the cross-section of the liquid changes as it moves from the cylindrical portion of the syringe through its tapering conical section at the outlet, the liquid's velocity increases as it is forced out of the syringe. Should an uncharacteristic resistance be perceived during an injection into a catheter, care must be taken that a blood clot is not being dislodged. Blood thinning agents would then have to be administered or, alternatively, if the clot is still perceived connected to the catheter, the catheter should be removed in favor of a new catheter. When a "long line" catheter system is used, appreciable time and resources of the hospital staff will have been required to reinstall the long line, which sometimes spans from a patient's leg into the patient's heart.

The following prior art reflects the state of the art of which applicant is aware and is included to discharge applicant's acknowledged duty to disclose relevant prior art. It is respectfully submitted, however, that none of the patents teach singly nor render obvious when considered in any conceivable combination the nexus of the instant invention as set forth in detail hereinafter and claimed with specificity.

| PATENT NO. | ISSUE DATE | INVENTOR |
|---|---|---|
| U.S. PATENT DOCUMENTS | | |
| 1,643,531 | September 27, 1927 | Wolf |
| 1,762,430 | June 10, 1930 | Tokita |
| 2,667,165 | January 26, 1954 | Smith |
| 2,667,872 | February 2, 1954 | Smith |
| 2,744,527 | May 8, 1956 | Barrett, et al. |
| 2,744,528 | May 8, 1956 | Barrett, et al. |
| 2,748,770 | June 5, 1956 | Moeck |
| 2,768,623 | October 30, 1956 | Marchand |
| 2,911,972 | November 10, 1959 | Elinger |
| 3,078,847 | February 26, 1963 | Wendell, et al. |
| 3,089,489 | May 14, 1963 | Dunmire |
| 3,335,914 | August 15, 1967 | Strazdins, et al. |
| 3,340,869 | September 12, 1967 | Bane |
| 3,557,788 | January 26, 1971 | Swartz |
| 3,712,295 | January 23, 1973 | Kline |
| 3,736,933 | June 5, 1973 | Szabo |
| 4,018,222 | April 19, 1977 | McAleer, et al. |
| 4,130,117 | December 19, 1978 | Van Eck |
| 4,168,032 | September 18, 1979 | Sneider |
| 4,282,986 | August 11, 1981 | af Ekenstam, et al. |
| 4,357,937 | November 9, 1982 | Burrell, Jr., et al. |
| 4,411,656 | October 25, 1983 | Cornett, III |
| 4,548,601 | October 22, 1985 | Lary |
| 4,610,670 | September 9, 1986 | Spencer |
| 4,753,638 | June 28, 1988 | Peters |
| 4,955,871 | September 11, 1990 | Thomas |
| 4,994,039 | February 19, 1991 | Mattson |
| 5,102,398 | April 7, 1992 | Farris |
| FOREIGN PATENT DOCUMENTS | | |
| FR 470,700 | April 7, 1914 | Viviez |
| DT 446,819 | July 7, 1927 | Gaertner, et al. |
| DT 556,491 | August 10, 1932 | Meyer |
| GB 557,400 | November 18, 1943 | Wirth |
| FR 1,316,596 | December 26, 1962 | Bouet |
| AU 278,032 | December 2, 1965 | Williams, et al. |
| FR 2,058,585 | May 28, 1971 | Lomenie |
| DE 3827335 A1 | February 15, 1990 | Ruff, et al. |

SUMMARY OF THE INVENTION

The instant invention has certain attributes which distinguish itself over the known prior art. Viewed from one perspective, the syringe according to the present invention is not a two piece system since it does not involve a piston and cylinder arrangement in a conventional sense; rather it is a one piece system formed as a container having walls which can deform in a controlled fashion to dispense liquid.

Ideally, the liquid contained within the syringe is prefilled at a site remote from the administration of the dose to a patient. Typically the syringe is prefilled at a pharmaceutical factory. As a result, there is no intermediate step where one is required to fill a syringe from an ampoule. There is thus no need to transport the syringe with its needle connected until it is time to administer the dose. When a catheter is used, no needle is even required because the luer coupling of the syringe can dock with a complemental fitting on the catheter.

The walls of the syringe collapse when ejecting the fluid. The syringe does not lend itself to multiple or subsequent reuses since the final configuration of the syringe is collapsed. Refilling the syringe would be analogous to trying to "get toothpaste back into a toothpaste tube".

Because the syringe is prefilled, it can be labeled with the contents of the medication. Thus, the chances of transposing syringes and administering an inappropriate dose to a patient will have been minimized.

In its most elemental form, the instant invention includes a bellows-type diaphragm at one end. The diaphragm serves as a main reservoir for the fluid. The reservoir communicates with a tapering section which ultimately communicates with a luer-type coupling. The coupling has an outlet which has been temporarily placed in fluid communication with a conduit which in turn leads to a chamber. A portion of the chamber may include a tab member thereon provided with indicia correlative of the fluid within the syringe. The area where the luer outlet connects to the conduit is provided with a scoreline or other weakened area. This facilitates the removal of the conduit and chamber from the remainder of the syringe. Preferably, sufficient liquid is present within the interior of the device so that liquid will reside initially within both the reservoir and at least a portion of the chamber.

Air is naturally present when a liquid is filled into a container. Gas such as air will naturally travel with the liquid when it is being placed into the syringe at the factory, since handling of the liquid naturally implicates some aeration as a natural consequence of fluid handling in an automated environment. Moreover, even if it were economically feasible to fill a device without the presence of any air, the costs associated with processing the liquid prior to inclusion within the syringe would involve a needless expense, because the liquid would have to be deaerated and the manufacturing process would have to be in a substantially airfree environment. The air must be accounted for and dealt with when prefilling syringes.

Even though airless liquid can be developed by introducing the liquid in an evacuated (vacuum) environment, it is needlessly expensive. Moreover, shipping of the syringe can include pressure change (such as during air transport) with the syringe. In turn, this can induce air back into the device since most FDA approved plastic which would be suitable candidates for blow molding this syringe will still allow some air seepage either as a function of time or by virtue of pressure differential. Even though seepage is small it should be recognized as a potential problem.

Assume that the syringe has been prefilled at a factory such that sufficient liquid is present to occupy the entire reservoir and all of the tapering section, conduit and at least a portion of the chamber. With the syringe oriented so that the chamber is at a higher elevation than the reservoir, the syringe system can be "burped" to induce all air into the chamber prior to severing the conduit and chamber from the syringe at its luer opening. In this way, the thus formed syringe is devoid of all gas and is now ready for utilization. Other versions are disclosed which can purge air in other analogous manners.

The structure of the instant invention involves an appreciable step down in the ratio of syringe diameter at its widest (i.e. storage reservoir) compared to its luer type outlet. Typically this ratio involves a large diameter (20–50 mm.) to a small diameter (0.1–1 mm.). The result is greater sensitivity to the presence of obstructions down stream (e.g. clotting) the outlet (e.g. in a catheter) because of the liquid resistance "amplification" due to the pressure/velocity changes.

OBJECTS OF THE INVENTION

Accordingly, it is a primary object of the present invention to provide a useful and novel prefilled syringe.

It is a further object of the present invention to provide a device as characterized above including a reservoir, a chamber in fluid communication with the reservoir by means of a flow path, outlet means interposed between the chamber and the reservoir and in the flow path allowing the fluid communication between the chamber and the reservoir, and means to disassociate the reservoir and outlet from the chamber.

It is a further object of the present invention to provide a prefilled syringe which takes into account the manufacturing realities of the inclusion of air or other gas during the filling process.

It is a further object of the present invention to provide a device as characterized above which is extremely sensitive to tactile feedback to provide an indication of an unwanted obstruction during the injection process.

It is a further object of the present invention to provide a device as characterized above which has a relatively small footprint and allows itself to be economically molded, nested and stored.

It is a further object of the present invention to provide a device as characterized above which minimizes the possibility of an inadvertent needle stick by minimizing the scenarios during which the utilization of a needle is required.

It is a further object of the present invention to provide a device as characterized above which is so constructed as to discourage the likelihood of reuse by the syringe having been collapsed after its initial use.

Viewed from a first vantage point, it is an object of the present invention to provide a method for dispensing medication, the steps including diagnosing a need for medication, prescribing a specific medication for the need, selecting a syringe that has been prefilled with the specific medication, orienting the syringe such that its liquid reservoir is at a lowermost elevation, an air chamber is at a highest elevation and an outlet of the syringe is at an elevation intermediate the reservoir and air chamber, burping the syringe to force all air into the air chamber, separating the air chamber from the reservoir at the outlet, and administering the medication through the outlet.

Viewed from a second vantage point, it is a further object of the present invention to provide a method for forming and prefilling a syringe, the steps including: forming a mold wall to define an enclosed volume having a syringe reservoir, a chamber, and a syringe outlet area interposed between the syringe reservoir and chamber, introducing a plastic into the mold, forcing the plastic to contact the wall of the mold leaving a hollow central area and a thin outer shell defining the syringe, chamber and outlet area, introducing medication into the shell to fill most of the enclosed volume defined by the reservoir, outlet area and the chamber, and sterilizing the prefilled syringe and medication.

These and other objects will be made manifest when considering the following detailed specification when taken in conjunction with the appended drawing figures.

DESCRIPTION OF PREFERRED EMBODIMENTS

Referring to the drawings now, wherein like reference numerals refer to like parts throughout the various drawing figures, reference numeral 10 is directed to the prefilled syringe according to one form of the present invention.

Figure 10:
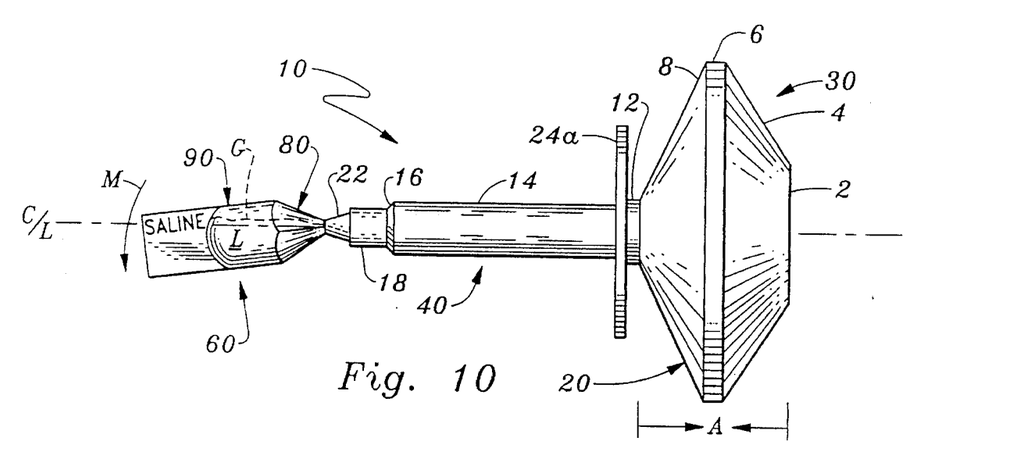
FIG. 10 is a view of one end of the FIG. 1 cap before severing.
Figure 11:
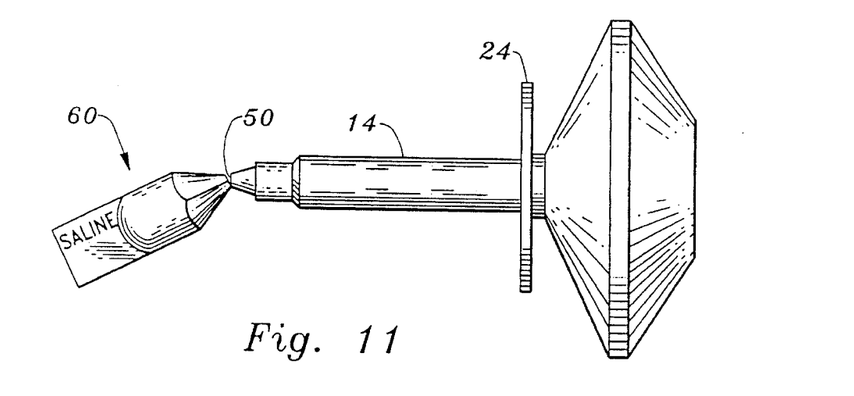
FIG. 11 is a view of one end of the FIG. 1 cap at severing.
Figure 12:
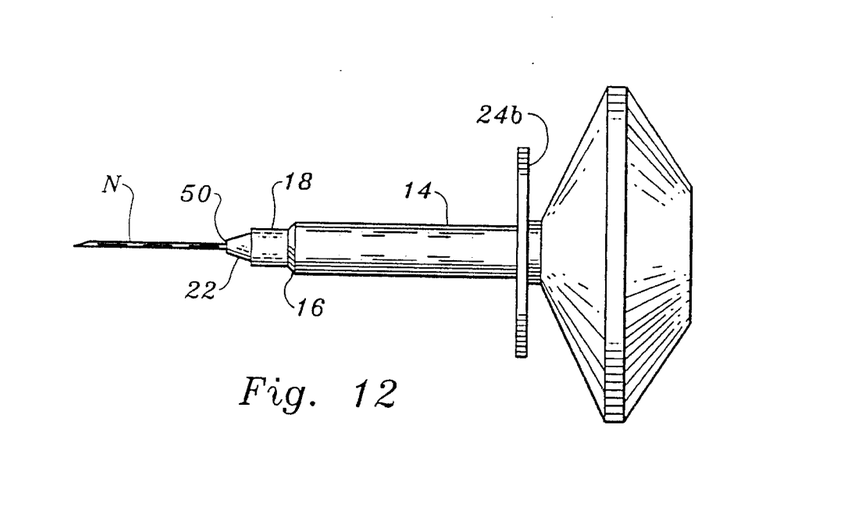
FIG. 12 is a view of one end of the FIG. 1 cap after severing.

In its essence, and particularly with respect to FIGS. 10 through 12, the syringe 10 includes a reservoir 30 which is in operative fluid communication with a scored outlet 50. The outlet 50 in turn communicates with a conduit 80 that leads to a chamber 90. A tab portion 100 extends from chamber 90 at an end remote from conduit 80. Collectively, the tab 100, chamber 90 and conduit 80 form a type of cap 60 which protects the outlet 50 until the cap 60 is severed from the outlet 50 via the scoreline.

In use, the tab will include indicia thereon correlative of a liquid contained within the prefilled syringe. This makes it more likely that only a proper liquid will be dispensed to the appropriate patient. Once the need for the liquid has been determined, a sequencing operation shown in FIGS. 2 through 4 will be effected. First, the syringe is oriented such that the chamber 90 and tab 100 is at a higher horizontal elevation compared to the reservoir 30 which is at a lower elevation. Next, the syringe 10 is manipulated to assure that all gas bubbles will have migrated up into the air chamber 90. This may be accelerated by tapping the syringe or "burping" the syringe.

Figure 3:
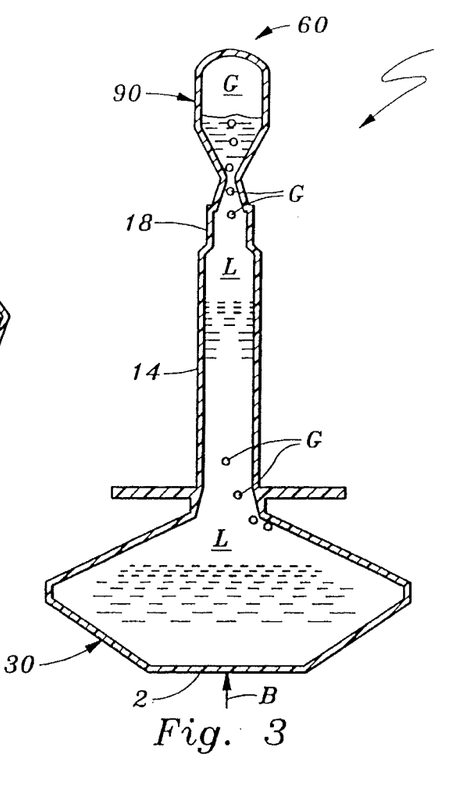
FIG. 3 is a schematic depiction of FIG. 1 manipulated in a second way.
Figure 4:
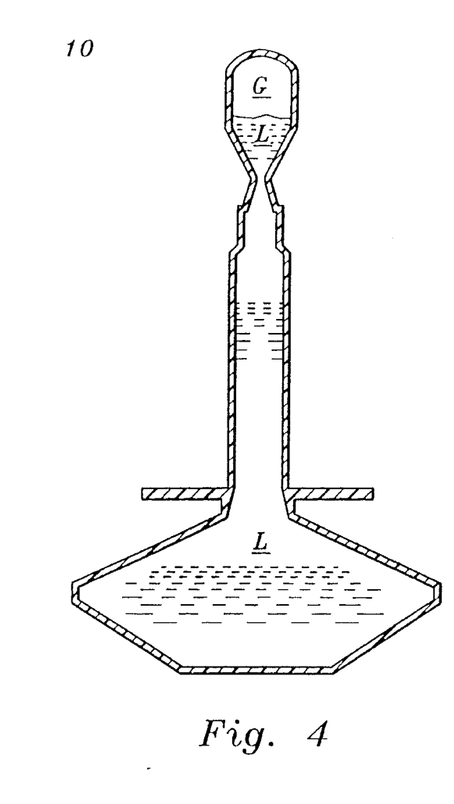
FIG. 4 is a schematic depiction of FIG. 1 manipulated in a third way.
Figure 5:
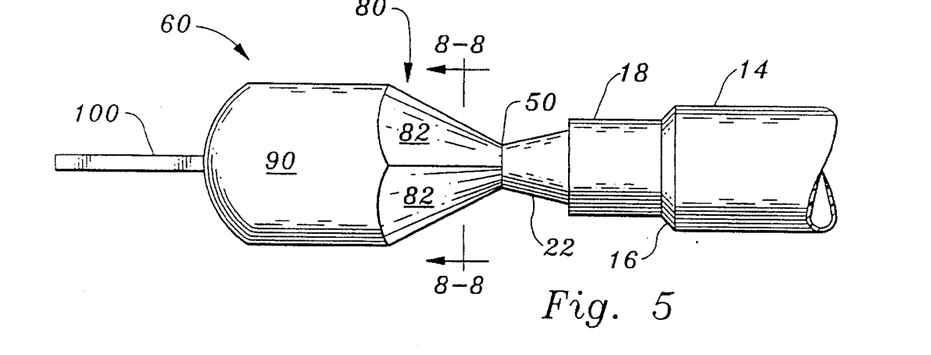
FIG. 5 is a view of one end of the FIG. 1 cap before severing.
Figure 6:
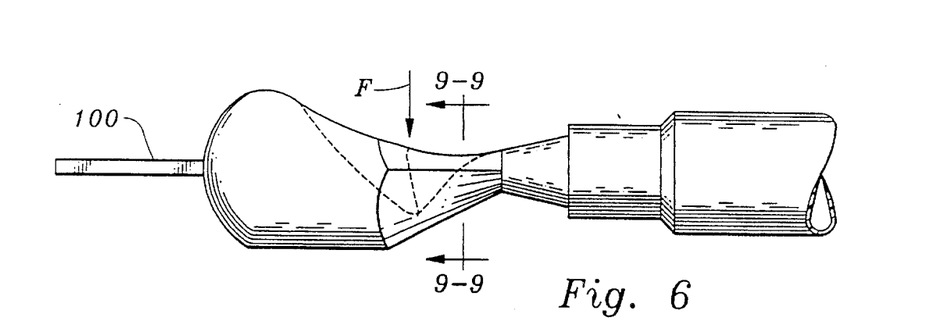
FIG. 6 is a view of one end of the FIG. 1 cap near severing.

It is expected that sufficient liquid will be contained within the prefilled syringe so that when oriented as shown in FIGS. 3 and 4, the liquid contained within the syringe will extend partly into the air chamber 90 and that a visually discernible meniscus exists between gas and the liquid. Preferably, all gas is to be located and confined to the chamber prior to syringe use. At this point, and referring to FIG. 11, the syringe is dissociated from the chamber 90 at the scoreline of outlet 50. The outlet 50 is now adapted to be used in any of several fashions. FIG. 12 reflects an environment where a conventional hypodermic needle is disposed on the luer-type coupling defining the outlet 50. Another scenario involves having the luer-type coupling outlet 50 operatively coupled to a catheter for subsequent infusion into a patient.

More particularly, and particularly with respect to FIGS. 10 through 12, the following characteristics of the prefilled syringe 10 can be observed. The right-hand side portion of FIG. 10 shows a reservoir 30 formed somewhat as a bellows-type diaphragm 20. The reservoir 30 encompasses an enclosed volume formed by an end wall 2 which has a circular outer periphery that leads to a conically diverging wall 4. The wall 4 communicates with an annular band 6 at one edge thereof. Thereafter, a second edge of the annular band 6 opposite from the diverging wall 4 transitions to a conically converging wall 8 which terminates in a cylindrical section 12 having a constant cross-section and is oriented such that its axial center is coincident with a center of end wall 2.

The cylindrical section 12 communicates with a finger purchase area 24 which allows one's fingers to be placed on a first face 24a of the purchase area 24 remote from the end wall 2 so that a contracting motion along the direction of the arrows "A" will cause the reservoir to compress, forcing liquid from the cylindrical section 12 and diaphragm 20. The finger purchase 24 is substantially disc-shaped and has a hollow central area which allows communication between the cylindrical section 12 and a first tubular section 14 located on the first face side 24a of the purchase area 24 and coaxial with end wall 2 and cylindrical section 12. First tubular section 14 has a smaller diameter than cylindrical section 12. An end of the tubular section 14 remote from the finger purchase 24 has a tapered portion 16 that leads to another second tubular section 18 having substantially constant circular cross-section, axially aligned with but of a lesser diameter than the first tubular section 14. First and second tubular sections 14, 18 collectively can define a cannula portion 40 (FIG. 10). This second tubular section 18 necks-down to an axially aligned converging cone 22 that terminates in the outlet 50 configured as a luer coupling. Initially, the luer coupling outlet 50 is defined as a scoreline or weakened area.

Figure 1:
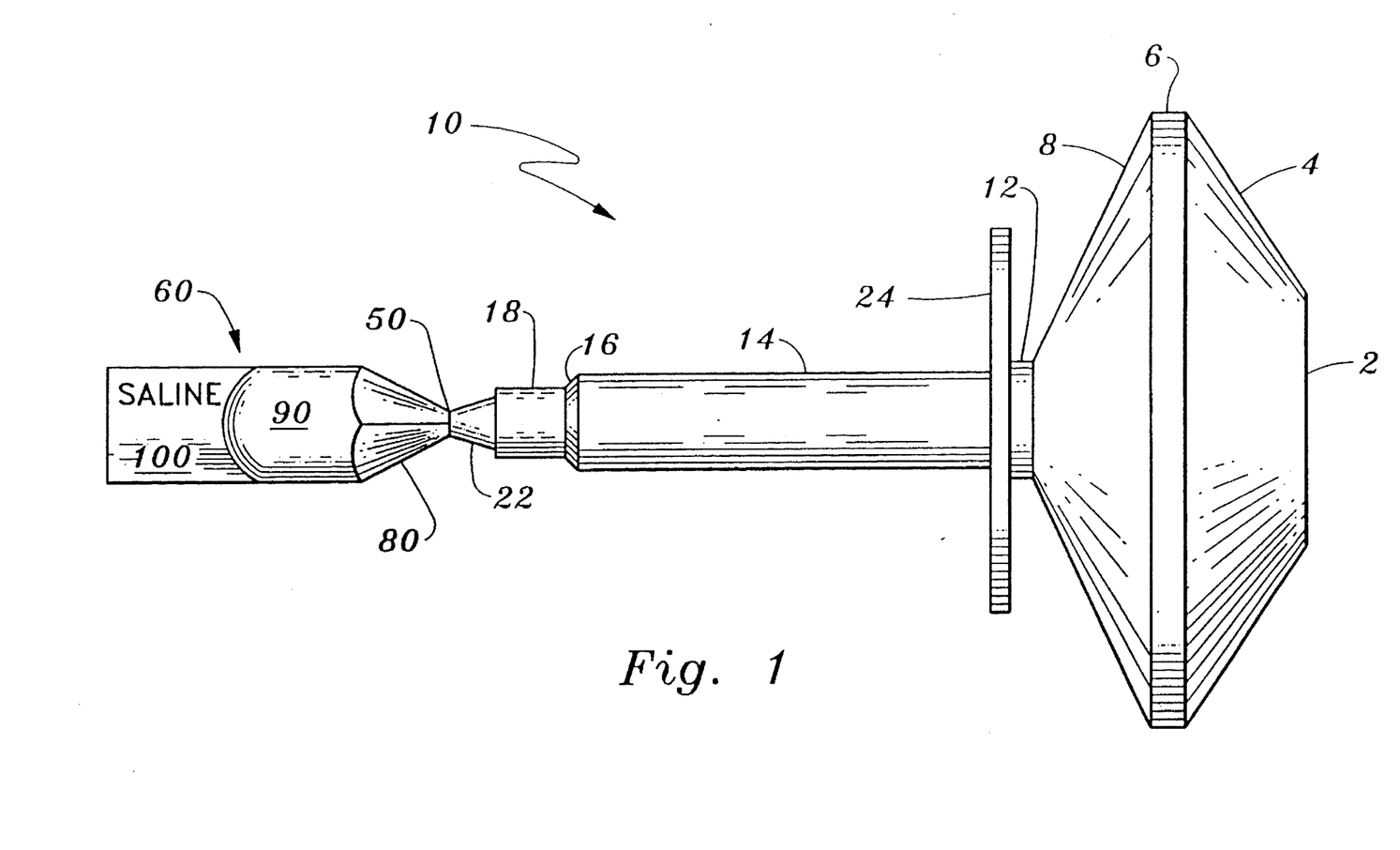
FIG. 1 is a side view of the prefilled fluid syringe according to one form of the present invention.

Cone 22 thereafter communicates with conduit 80. Tab 100 is integrally formed with chamber 90 which communicates with conduit 80. Tab 100, chamber 90 and conduit 80 collectively define a cap 60 prior to severing from outlet 50. FIGS. 10 and 11 show a severing sequence. Initially, the syringe appears as in FIG. 1. Bending moment M, by applying force to the cap 60 about center line C/L, causes fracture of the conduit 80 from cone 22 at scoreline 50 (FIG. 11). FIG. 12 shows a needle N installed.

FIGS. 5 through 9 provide details with respect to one form of the conduit 80, air chamber 90 and tab 100. Conduit 80 is formed with plural facets 82. As can be shown in FIG. 5, preferably facets 82 of the conduit 80 diverge away from the luer coupling outlet 50. The converging cone 22 is shown as having a gradually changing diameter along its axial extent. A multiplicity of facets 82 define the conduit 80 which expands toward the chamber 90. The intent of the facets is to provide one way to crimp the conduit 80 upon severing. Thus, the additional liquid associated with chamber 90 remains within the chamber 90 rather than seeps out via the conduit 80 after the conduit 80 and chamber 90 have been severed at the outlet 50. Stated alternatively, should the capillary attraction in conduit 80 be too small to retard liquid from leaking out of the chamber 90, a means to constrict the conduit 80 by pinching and deforming the conduit 80 is shown.

Figure 7:
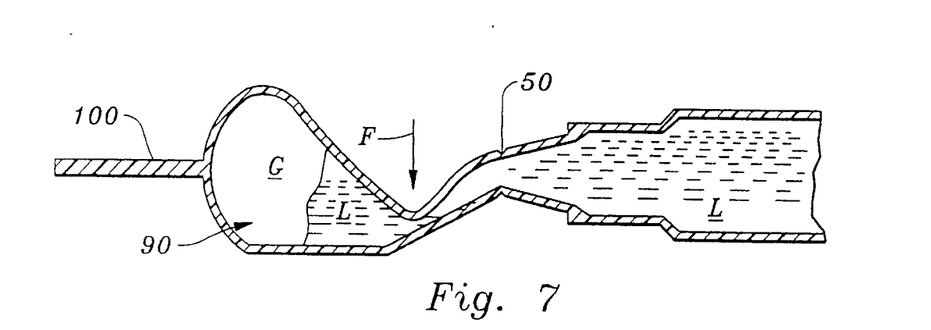
FIG. 7 is a view of one end of the FIG. 1 cap during severing.
Figure 8:
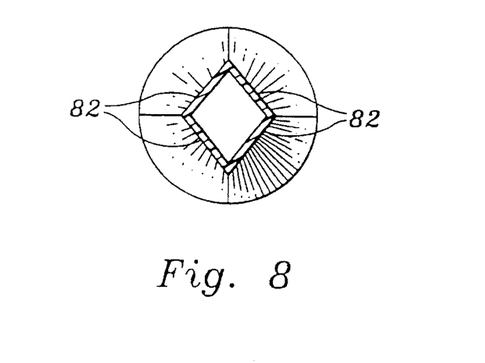
FIG. 8 is a sectional view along lines 8—8 of FIG. 5.
Figure 9:
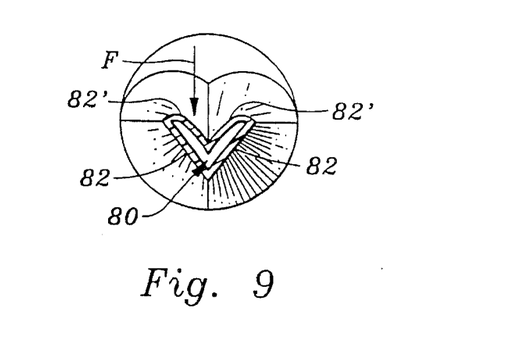
FIG. 9 is a sectional view along lines 9—9 of FIG. 6.

One form of constriction is shown in FIG. 9. Four facets are shown in section in FIG. 8 oriented in a diamond pattern. Two facets 82 from FIG. 8 have been distorted by a force along the direction of the arrow "F" in FIG. 9 to provide a narrow "heart" shaped constrictive opening. In this manner, the tendency of the liquid to flow outside the conduit 80 will have been impeded. As shown in FIG. 9, the "top" portions of the facets 82' have been distorted into arcuate segments so that the opening 80 is somewhat V-shaped. FIG. 7 illustrates that the liquid L as well as the gas reside within the chamber 90 just prior to severing at the outlet 50.

Figure 2:
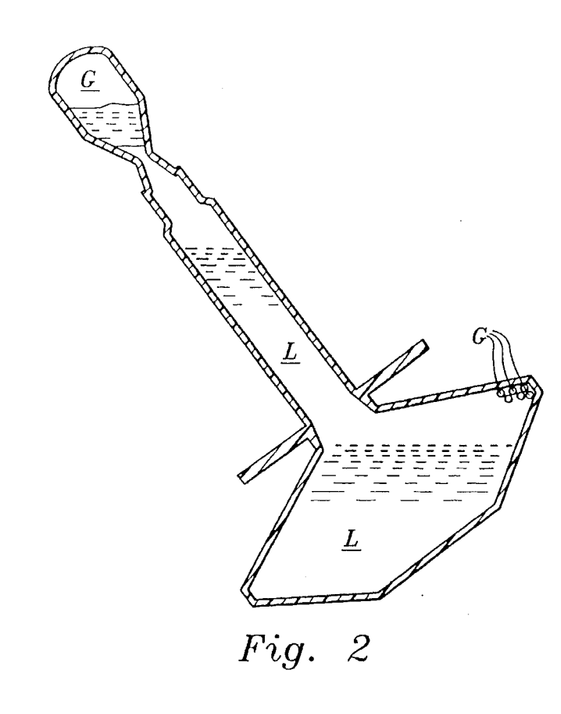
FIG. 2 is a schematic depiction of FIG. 1 manipulated in a first way.

FIGS. 2 through 4 illustrate diagramatically how the syringe will be purged of all resident gas G and directed to the chamber 90 of the cap 60. It is to be noted that pressure differentials can cause the plastic used in formulating the syringe to admit some gases after manufacture. However, even in the most stringently controlled manufacturing processes, gas is a normal by product when filling containers with liquid and must therefore be taken into account. According to the present method and apparatus, the entrained gas can be directed into the chamber 90 and removed from the liquid contained both within the reservoir 30 and the tubular sections 14, 18.

As shown in FIG. 3, once the syringe 10 has been oriented such that the chamber 90 is at a higher horizontal elevation than the reservoir 30, it may be desirable to provide a burping force B on a wall of the reservoir, such as at end wall 2. The syringe could also be tapped to move gas into chamber 90. When either occurs, there will be a natural tendency of the gas bubbles G to migrate from the reservoir 30, through the tubular sections 14, 18 and then upward into the chamber 90. Because these syringes are formed from a class of plastic materials which are optically transparent, it is possible to perceive the presence of gas within the body of the syringe 10. Thus, this manipulative procedure of burping or tapping the syringe can be quite effective.

Assume that the FIG. 12 configuration has been achieved with a syringe needle N deployed on the luer outlet coupling 50. In some situations, especially during an intravenous injection, it may be desirable to assure that a vein has been penetrated. This occurs usually in the prior art by retracting a syringe plunger slightly to draw blood back into the portion of the syringe 10 at least to the converging conical section 22 or the second tubular section 18.

Figure 13:
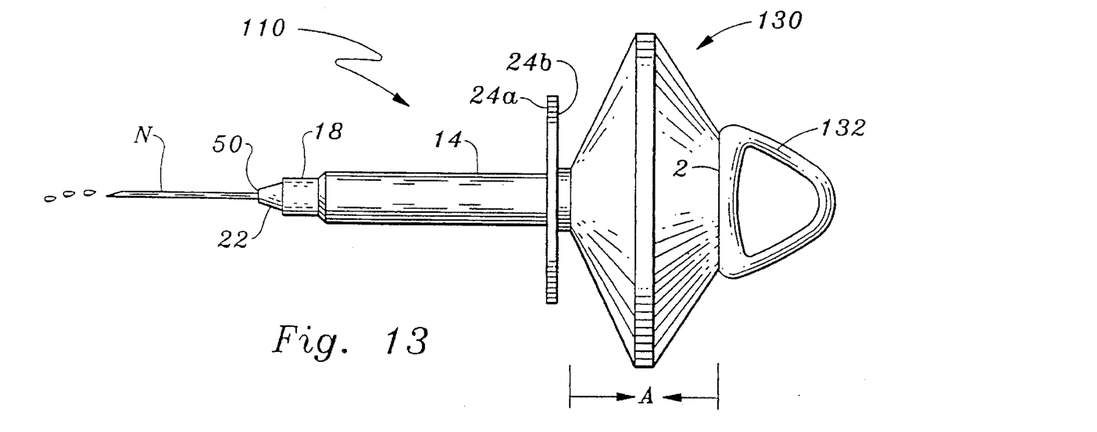
FIG. 13 is a side view of a second embodiment.

The embodiment of FIG. 13 lends itself to such a manipulation. A modified form of syringe 110 is shown where reservoir 130 has been changed. In essence, the modified reservoir 130 includes an end wall 2 similar to the previously discussed embodiment, but also includes compression assisting means in the form of a substantially "D-shaped" pull ring 132. In use and operation, the dose administrator will place the fore finger and mid finger of one hand on an outer surface 24a of the finger purchase 24 and the thumb will be placed within the D-ring 132. First, by providing pressure in the direction of the arrows "A" shown in FIG. 13, a slight compression of the reservoir bellows 20 will allow a small amount of liquid to be burped from the needle N to assure that liquid is present within the entire cavity of the needle. It is possible thereafter to provide the injection into the vein with the assurance that no air exists. Next, after the needle has been inserted, the fore finger and middle finger are placed on side 24b of purchase area 24 to move the bellows 20 opposite arrow "A" to draw blood back into conical section 22.

Figure 14:
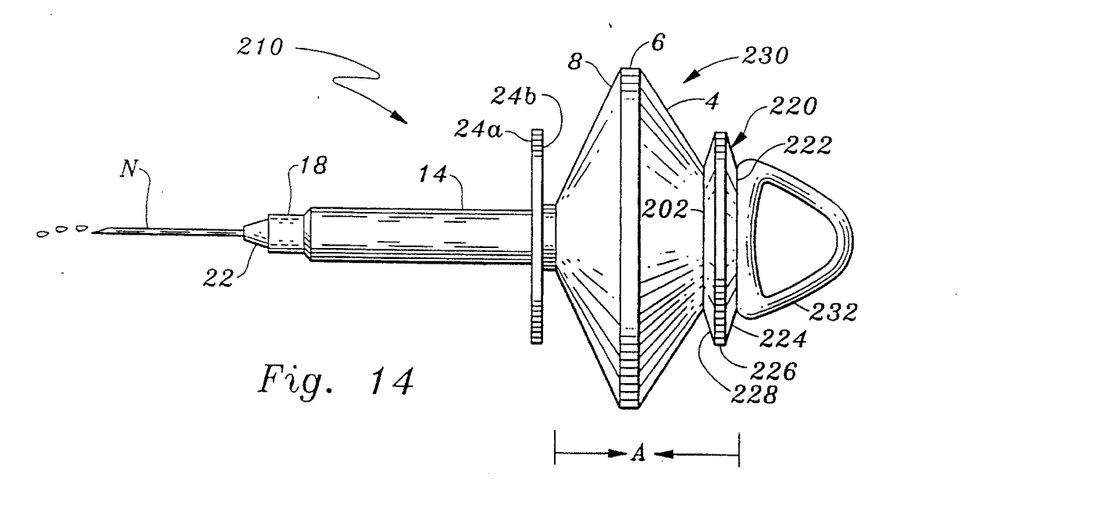
FIG. 14 is a side view of a third embodiment.

Another embodiment of syringe 210 is shown in FIG. 14. There, the modified reservoir 230 includes a D-shaped ring 232, but has a "mini-bellows" 220 interposed between the main bellows 230 and the D-ring 232. The mini-bellows 220 includes an annular band 226 coupled to a mini-bellows converging wall 228 that connects with what heretofore was (in previous embodiments) an end wall 2, but now is an opening 202 in fluid communication with the interior of the reservoir 230. In other words, diverging wall 4 connects to converging wall 228. A mini-bellows diverging wall 224 is connected to band 226 on a side opposite converging wall 228. Wall 224 is sealed off with an end wall 222. In turn end wall 222 supports D-ring 232 so that a "two stage" bellows-diaphragm will have been provided. Thus, bellows 220 and 230 each contain fluid and are in communication at their juncture.

In this embodiment, the needle end can be purged of all air by providing the pressure in the direction of the arrows "A" between front face 24a of the finger purchase 24 and with the thumb inserted in the D-ring 232 as shown in FIG. 14. The structure of the mini-bellows 220 is preferably programmed to "snap" into a first, collapsed position more readily. Therefore, when force is applied along arrow "A", the needle is purged. The syringe is then ready for insertion into a vein. Once the syringe has been inserted into the vein, that fact can be corroborated by moving one's fore finger and middle finger to an opposite side 24b of the finger purchase 24 and providing a force opposite from the direction of the arrow "A" to retract the D-ring back to its original FIG. 14 configuration. At this point, blood will be visually drawn into the cone section 22 and tubular section 18 and 14 if a vein has in fact been accessed.

Any of the bellows, such as the mini-bellows 220 can be programmed to collapse more readily than the other bellows by altering certain design variables such as the dimension (width) of the annular band portion (e.g. 226 visa vis 6), the slope of the walls 224, 228 (visa vis 4, 8) or perhaps thickness gradations in the plastic itself visa vis other areas. With this version, burping or tapping air into cap 60 is not critical since after severing, opening 50 can burp out gas.

Figure 15:
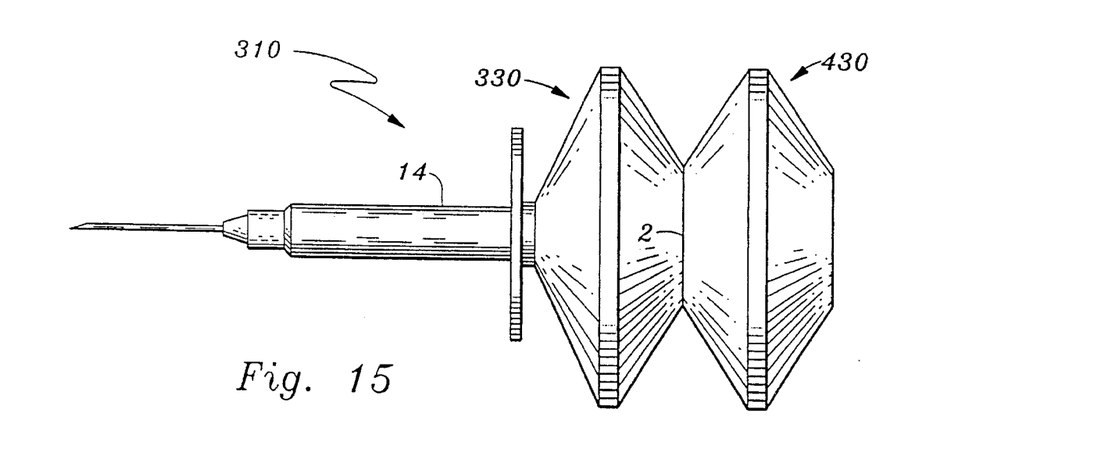
FIG. 15 is a side view of a fourth embodiment.

FIG. 15 illustrates another scenario in which acute cardiac patients can be treated with premeasured sequential doses of liquid. For example, during cardiac arrest, it is preferred to administer liquid (e.g. epinephrine) in incremental doses directly into the heart. Heretofore, successive syringes were required to have been loaded in order to provide sequential doses. With the FIG. 15 embodiment 310 a series of bellows, e.g. a first bellows reservoir 330 is sequentially linked in fluid communication to a second bellows reservoir 430 so that successive doses can be administered as the need arises. In view of the FIG. 15 environment, several doses (i.e. in excess of the two reservoirs shown) could be thusly stacked in series. As mentioned above with FIG. 14, the reservoirs can be preprogrammed to collapse in a desired sequence to provide different volumes of liquid.

In use and operation, it is contemplated that first a need for medication will have been diagnosed by the medical practitioner. Next the specific medication for the diagnosed need will have been prescribed. Third a syringe will have been selected which has been prefilled with the specific medication. Fourth the syringe is then oriented such that its liquid reservoir is at a lowermost elevation and an air chamber is at a highest elevation such that the outlet of the syringe is at an elevation intermediate the reservoir and the air chamber. Next, the syringe is burped or in other ways encouraged to force all of the air into the chamber. Next, the air chamber is separated from the reservoir at the outlet and finally the medication is administered through the outlet. This administration can take the form of communication with the syringe or a catheter for example.

With the FIG. 14 embodiment, the cap 60 could be first severed before burping out all (or some of) the gas from the syringe interior. Filling the needle and purging out gas could utilize the liquid in the mini-bellows 220.

Figure 16:
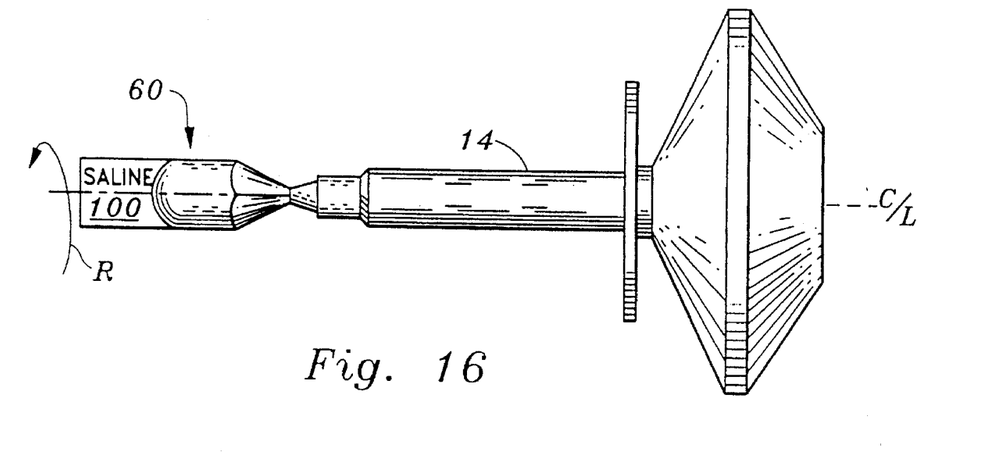
FIG. 16 is a view of one end of the FIG. 1 cap before severing.
Figure 17:
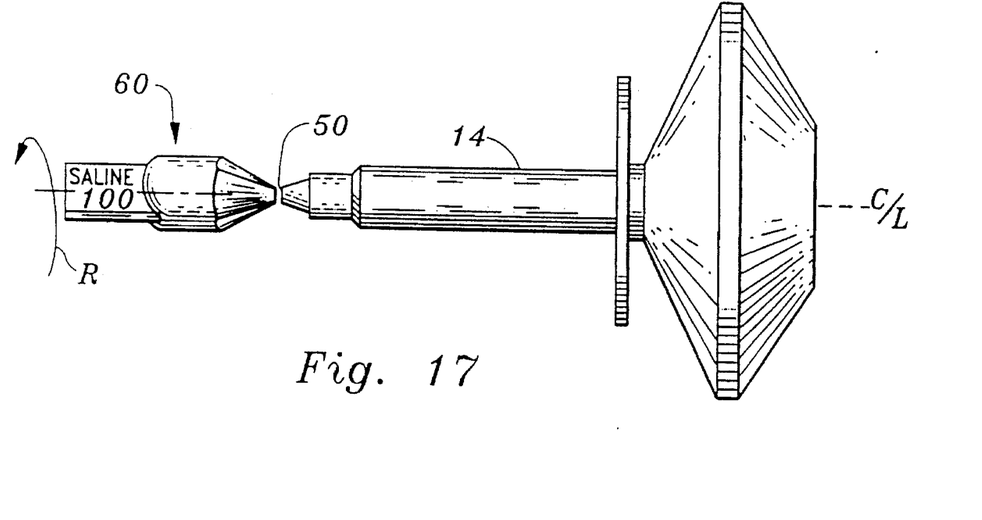
FIG. 17 is a view of one end of the FIG. 1 cap during severing.

FIGS. 16 and 17 reveal a further method of freeing the cap 60 from the body of the syringe at outlet 50. As shown, a rotational force R can be applied (optimally at the tab 100) to twist the cap 60 off from the outlet 50. As shown, the plastic forming the luer coupling at outlet 50 can be programmed for minimal deformation while the cap end (adjacent conduit 80) will have been twisted to a constricted opening. A combination of cutting, rotating, bending and flexing could also be used to remove the cap 60 as described above.

Moreover, in view of the foregoing, it should be apparent that numerous structural modifications and adaptations can be resorted to without departing from the scope and fair meaning of the instant application as set forth hereinabove and as defined hereinbelow by the claims.

I claim:

1. A syringe comprising, in combination:

a reservoir, a chamber in fluid communication with said reservoir by means of a flow path, outlet means interposed between said chamber and said reservoir and in said flow path allowing the fluid communication between said chamber and said reservoir, gas and liquid in said syringe, with enough liquid to fill said reservoir and said flow path, but only partially fill said chamber to accommodate gas therein, and means to disassociate said reservoir and outlet means from said chamber.

2. The syringe of claim 1 wherein said means to disassociate said reservoir and outlet from said chamber includes a scoreline.

3. The syringe of claim 2 wherein said outlet once severed defines a luer coupling.

4. The syringe of claim 3 wherein said chamber includes an indicia means on a portion thereof remote from said outlet means to indicate the contents within the syringe.

5. The syringe of claim 4 wherein said reservoir is formed as a first bellows-type diaphragm having an end wall having a substantially circular periphery, a diverging wall extending outwardly from said periphery of said end wall, an annular band extending from said diverging wall remote from said end wall, and a converging wall extending from an edge of said annular band remote from said diverging wall, said reservoir provided with fluid contained therewithin.

6. The syringe of claim 5 wherein a finger purchase is fixed on said syringe intermediate said diaphragm and said outlet for facilitating manipulation of the syringe.

7. The syringe of claim 6 including a first tubular section extending between said finger purchase and said outlet.

8. The syringe of claim 7 including a compression means on an end of said diaphragm remote from said finger purchase to collapse said diaphragm.

9. The syringe of claim 8 wherein a second bellows-type diaphragm is interposed between said compression means and said first diaphragm.

10. The syringe of claim 5 wherein a second bellows-type diaphragm is sequentially in fluid communication with and serially disposed to said first bellows-type diaphragm.

11. The syringe of claim 10 wherein a D-ring is placed on an end of said second diaphragm remote from said outlet.

12. The syringe of claim 4 wherein said chamber includes a conduit extending between said chamber and said outlet means.

13. The syringe of claim 12 wherein said conduit includes a plurality of facets deformable to constrict the conduit opening.

14. A syringe having a liquid reservoir and a gas/liquid chamber, said chamber spaced from said reservoir by a flow path and held in fluid communication therewith, and the syringe formed by:

forming a mold wall to define an enclosed volume having the liquid reservoir, the chamber, and a syringe outlet area interposed between the liquid reservoir and chamber along the flow path, introducing a plastic into the mold, forcing the plastic to contact the wall of the mold leaving a hollow central area and a thin outer shell defining the reservoir, the chamber and flow path, introducing liquid into the shell to fill most of the enclosed volume defined by all of the reservoir and flow path and at least some of the chamber, sealing the syringe, and sterilizing the prefilled syringe and liquid.

15. The syringe of claim 14 used by:

orienting the syringe such that said liquid reservoir is at a lowermost elevation, said chamber is at a highest elevation and said outlet area of the syringe is at an elevation intermediate said reservoir and the chamber, manipulating the syringe to force all air into the chamber, separating the the chamber from the reservoir at the outlet area, and administering the liquid through the outlet.

16. The syringe of claim 15 including administering the liquid by installing a needle on the outlet of the syringe, and purging the needle of gas.

17. The syringe of claim 16 including inserting the needle of the syringe into a vein and withdrawing blood from the vein to verify proper placement of the needle.

18. The syringe of claim 17 including providing successive doses by incrementally compressing a series of liquid reservoirs.

19. The syringe of claim 18 including forming a weakened area immediately adjacent the outlet area to aid in severing the chamber from the syringe at the outlet area by stressing the outlet area and severing it.

20. The syringe of claim 19 including forming a purchase area for one's fingers integral to the syringe to facilitate in manipulating the liquid within the syringe.

21. A plungerless syringe configured as a deformable diaphragm, an air/liquid chamber, and a fluid path interposed between said diaphragm and said chamber, including an outlet formed in said fluid path, liquid in the syringe to fill the diaphragm and fluid path and at least a portion of the chamber, including using the syringe by, selecting a syringe that has been prefilled with a specific liquid, orienting the syringe such that its diaphragm is at a lowermost elevation, its chamber is at a highest elevation and an outlet of the syringe is at an elevation intermediate the diaphragm and said chamber, manipulating the syringe to force all said into the air chamber while only liquid remains in the diaphragm, separating the said chamber from the diaphragm at the outlet, and administering the liquid through the outlet.

22. The syringe of claim 21 including administering the liquid by installing a needle on the outlet of the syringe, and purging the needle of gas.

23. The syringe of claim 22 including inserting the needle of the syringe into a vein and withdrawing blood from the vein to verify proper placement of the needle.

24. The syringe of claim 23 including providing successive doses by incrementally compressing a series of liquid diaphragms.

25. Plungerless syringe, comprising:

a rearward end wall, a forward generally cylindrical and longitudinally extending cannula portion, a generally semi-spherical bellows portion attached to and decreasing in diameter toward said cannula portion, said bellows portion intermediate said rearward end wall and said cannula portion;

said bellows portion being hollow and providing an interior for receiving fluid and said cannula portion provided with a passageway extending longitudinally therethrough and in fluid communication with said interior;

said cannula portion including an outer end;

said bellows portion including a first bellows portion adjacent said end wall and providing a purge stage and upon said first bellows portion being collapsed by force acting inwardly against said end wall a portion of the fluid contained in the interior being expelled through the cannula portion passageway to purge air;

said end wall including means for being pulled rearwardly away from said cannula portion to cause intentional reflux of fluid into the cannula portion passageway to facilitate determination of the continuity of a fluid path including the interior;

said bellows portion including a second bellows portion intermediate said first bellows portion providing a flush stage upon the second bellows portion being collapsed by force acting inwardly against said end wall, fluid remaining in the interior after collapse of said first bellows portion being expelled through the cannula portion passageway;

said end wall having means to maintain said bellows portion collapsed to prevent intentional reflux of expelled fluid into said cannula portion passageway; and a removable tab member mounted to the outer end of the cannula portion for initially sealing the passageway to maintain the fluid in the interior and providing an over-fill chamber permitting the interior to be over-filled with fluid and providing head space isolated from the interior for receiving air contained in the fluid;

gas and liquid in said syringe, with enough liquid to fill said bellows portion and said cannula portion, but only partially fill said over-fill chamber to accommodate gas therein.

26. The plungerless syringe of claim 25 wherein said second bellows portion is provided with an external circumferential band for facilitating substantially uniform application of collapsing force to said second bellows thereby substantially preventing buckling of said second bellows portion during collapse and for maintaining said second bellows portion collapsed.

27. A syringe comprising, in combination:

a reservoir, a chamber in fluid communication with said reservoir by means of a flow path, outlet means interposed between said chamber and said reservoir and in said flow path allowing the fluid communication between said chamber and said reservoir, and means to disassociate said reservoir and outlet means from said chamber, wherein said means to disassociate said reservoir and outlet means from said chamber includes a scoreline, wherein said outlet means once severed defines a luer coupling adjacent said reservoir, wherein said chamber includes an indicia means on a portion thereof remote from said outlet means to indicate the contents within the syringe, wherein said chamber includes a conduit extending between said chamber and said outlet means, and wherein said conduit includes a plurality of facets deformable to constrict an opening formed on said conduit upon severing said outlet means.

28. A syringe comprising, in combination:

a reservoir, a chamber in fluid communication with said reservoir by means of a flow path, outlet means interposed between said chamber and said reservoir and in said flow path allowing the fluid communication between said chamber and said reservoir, and means to disassociate said reservoir and outlet means from said chamber, wherein said flow path between said chamber and said outlet means includes a conduit, and wherein said conduit includes a plurality of facets deformable to constrict a conduit opening formed upon severing said outlet means.

29. Syringe apparatus, comprising:

a cannula portion and a collapsible bellows portion, the cannula portion including a passageway extending therethrough and the bellows portion providing an interior in fluid communication with the passageway for receiving fluid which is expelled through the passageway upon collapse of the bellows portion, the cannula portion including an outer end;

a removable tab member mounted to the outer end of the cannula portion for initially sealing the passageway to maintain the fluid exclusively in the interior of the bellows and providing an over-fill chamber permitting the interior to be over-filled with both fluid and providing gaseous head space isolated from the interior for receiving air contained in the fluid; and gas and liquid in said syringe apparatus, with enough liquid to fill said bellows portion and said cannula portion, but only partially fill said over-fill chamber to accommodate gas therein.

30. Plungerless syringe, comprising:

a collapsible bellows including forward and rearward portions and providing an interior for receiving fluid and a cannula provided with a passageway in fluid communication with the interior and through which passageway fluid is expelled upon collapse of the bellows;

the bellows provided with a configuration causing said bellows portion to collapse upon being compressed;

the cannula including an outer end;

the bellows including a first bellows portion providing a purge stage and, upon the first bellows portion being collapsed, a portion of the fluid contained in the chamber is expelled through the cannula portion passageway to purge air;

the bellows portion including a second bellows portion providing a flush stage and upon the second bellows portion being collapsed the fluid remaining in the interior after collapse of the first bellows portion is expelled through the cannula portion passageway;

a removable tab member mounted to the outer end of the cannula portion for initially sealing the passageway to maintain the fluid in the interior and providing an over-fill chamber permitting the interior to be over-filled with fluid and providing head space isolated from the interior for receiving air contained in the fluid; and gas and liquid in said syringe, with enough liquid to fill said bellows and said cannula, but only partially fill said over-fill chamber to accommodate gas therein.

31. Plungerless syringe, comprising:

a rearward end wall, a forward generally cylindrical and longitudinally extending cannula portion, and a bellows portion intermediate said end wall and said cannula portion;

said bellows portion being hollow and providing an interior for receiving fluid and said cannula portion provided with a passageway extending longitudinally therethrough and in fluid communication with said interior;

said cannula portion including an outer end;

said bellows portion including a first bellows portion adjacent said rearward end wall and providing a purge stage and upon said first bellows portion being collapsed by force acting inwardly against said end wall, a portion of the fluid contained in the interior being expelled through the cannula portion passageway to purge air;

said rearward end wall being pulled rearwardly, away from said cannula portion to cause intentional reflux of fluid into the cannula portion passageway to facilitate determination of the continuity of a fluid path including the interior;

said bellows portion including a second bellows portion intermediate said first bellows portion providing a flush stage and upon the second bellows portion being collapsed by force acting inwardly against said rearward end wall, fluid remaining in the interior after collapse of said first bellows portion being expelled through the cannula portion passageway;

a removable tab member mounted to the outer end of the cannula portion for initially sealing the passageway to maintain the fluid in the interior and provide an over-fill chamber permitting the interior to be over-filled with fluid and providing head space isolated from the interior for receiving air contained in the fluid; and gas and liquid in said syringe, with enough liquid to fill said bellows portion and said cannula portion, but only partially fill said over-fill chamber to accommodate gas therein.

32. Plungerless syringe, comprising:

a collapsible bellows including forward and rearward portions and providing an interior for receiving fluid and a cannula provided with a passageway in fluid communication with the interior and through which passageway fluid is expelled upon collapse of the bellows;

the bellows provided with a configuration causing said bellows portion to collapse upon being compressed;

the cannula including an outer end;

the bellows including a first bellows portion providing a purge stage and upon the first bellows portion being collapsed a portion of the fluid contained in the interior is expelled through the cannula portion passageway to purge air;

the bellows portion including a second bellows portion providing a flush stage and upon the second bellows portion being collapsed, the fluid remaining in the interior after collapse of the first bellows portion is expelled through the cannula portion passageway;

means to maintain the bellows collapsed after collapse of both the first and second bellows portions;

a removable tab member mounted to the outer end of the cannula portion for initially sealing the passageway to maintain the fluid in the interior and providing an over-fill chamber permitting the interior to be over-filled with fluid and providing head space isolated from the interior for receiving air contained in the fluid; and gas and liquid in said syringe, with enough liquid to fill said bellows and said cannula, but only partially fill said over-fill chamber to accommodate gas therein.

* * * * *